United States Patent
Nebolsin et al.

(10) Patent No.: US 10,220,029 B2
(45) Date of Patent: *Mar. 5, 2019

(54) PHARMACEUTICAL COMPOSITION COMPRISING GLUTARIMIDE DERIVATIVES AND USE THEREOF IN THE TREATMENT OF EOSINOPHILIC DISEASES

(71) Applicant: OBSCHESTVO S ORGANICHENNOI OTVETSTVENNOSTIYU "PHARMENTERPRISES", Moscow (RU)

(72) Inventors: Vladimir Evgenievich Nebolsin, Moskovskaya Obl. (RU); Tatyana Alexandrovna Kromova, Kaluga (RU); Anastasia Vladimirovna Rydlovskaya, St. Petersburg (RU); Alexander Grigorievich Chuchalin, Moscow (RU)

(73) Assignee: OBSCHESTVO S OGRANICHENNOI OTVETSTVENNOSTIYU "PHARMENTERPRISES", Moscow (RU)

(*) Notice: Subject to any disclaimer, the term of this patent is extended or adjusted under 35 U.S.C. 154(b) by 0 days.

This patent is subject to a terminal disclaimer.

(21) Appl. No.: 15/844,703

(22) Filed: Dec. 18, 2017

(65) Prior Publication Data

US 2018/0104230 A1    Apr. 19, 2018

Related U.S. Application Data

(63) Continuation of application No. 15/036,603, filed as application No. PCT/RU2014/000855 on Nov. 12, 2014, now Pat. No. 9,949,962.

(30) Foreign Application Priority Data

Nov. 14, 2013 (RU) ................. 2013150861

(51) Int. Cl.
    *A61K 31/454* (2006.01)
    *C07D 211/88* (2006.01)
(52) U.S. Cl.
    CPC .......... *A61K 31/454* (2013.01); *C07D 211/88* (2013.01)
(58) Field of Classification Search
    CPC ..................... A61K 31/454; C07D 211/88
    See application file for complete search history.

(56) References Cited

U.S. PATENT DOCUMENTS 8,501,176 B2    8/2013    Koike
2016/0046598 A1  2/2016    Nebolsin et al.

FOREIGN PATENT DOCUMENTS

| EP | 2229935 A1 | 9/2010 |
|---|---|---|
| RU | 2378284 C2 | 1/2010 |
| RU | 2406727 C2 | 12/2010 |
| RU | 2013116826 A | 10/2014 |
| WO | 9424133 A1 | 10/1994 |
| WO | 9745448 A1 | 12/1997 |
| WO | 9901103 A2 | 1/1999 |
| WO | 03040164 A2 | 5/2003 |
| WO | 2007000246 A1 | 1/2007 |
| WO | 2007007054 A1 | 1/2007 |

OTHER PUBLICATIONS

Hogan SP et al. Eosinophils: biological properties and role in health and disease // Clin Exp Allergy; 38(5): 709-50, (2008).
Hofffman R., et al., Hematology: Basic Principles and Practice, 4th Ed. Philadelphia, Pa: Churchill Livingston; 768 (2005).
Blanchard C., et al., Biology of the eosinophil // Adv Immunol.; 101:81-121, (2009).
Bjornsson E., et al., Serum eosinophil cationic protein in relation to bronchial asthma in young Swedish population, Allergy; vol. 49: 730-736, (1994).
Noguchi H. et al., Tissue eosinophilia and eosinophil degranulation in syndroms associated with fibrosis // Am. J. Pathol. vol. 140, p. 521-528, (1992).
Barnes PJ., New drugs for asthma // Semin Respir Crit Care Med.; 33(6): 685-94, (2012).
Nair P., et al., Mepolizumab for prednisone-dependent asthma with sputum eosinophilia, NEJM., 360:985-93, (2009).

(Continued)

*Primary Examiner* — Umamaheswari Ramachandran

(74) *Attorney, Agent, or Firm* — Banner & Witcoff, Ltd.

(57) ABSTRACT

The present invention relates to novel biologically active glutarimide derivatives of general formula (I) or a pharmaceutically acceptable salt thereof, their use as a therapeutic agent for the treatment of eosinophilic diseases, preferably of allergic nature, in particular bronchial asthma, allergic rhinitis, polypous rhinosinusopathies, eosinophilic colitis, eosinophilic syndrome, allergic conjunctivitis, atopic dermatitis, Churg-Strauss syndrome, anaphylactic shock, Quincke's edema, eosinophilic vasculitis, eosinophilic esophagitis, eosinophilic gastroenteritis, or fibroses. The invention also relates to pharmaceutical compositions comprising glutarimide derivatives of general formula (I):

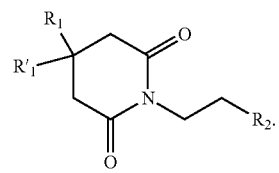

17 Claims, No Drawings

(56) References Cited

OTHER PUBLICATIONS

Haldar et al., Mepolizumab and exacerbations of refractory eosinophilic asthma, NEJM; 360: 973-84, (2009).

Gevaert P., Mepolizumab, a humanized anti-IL-5 mAb, as a treatment option for severe nasal polyposis, J Allergy Clin Immunol.; 128(5): 989-995, (2011).

Rothenberg ME et al., Treatment of patients with the hypereeosinophilic syndrome with mepolizumab. NEJM; 358 (12):1215-28, (2008).

Stein ML et al., Anti-IL-5 (mepolizumab) therapy for eosinophilic esophagitis, J. Allergy Clin Immuno.; 118(6):1312-9, (2006).

Kahn JE et al., Sustained response to mepolizumab in refractory Churg-Strauss syndrome, J. Allergy Clin Immunol., 125:267-70, (2010).

Kim S et al., Mepolizumab as a steroid-sparing treatment option in patients with Churg-Strauss syndrome, J Allergy Clin Immunol., 125:1336-43, (2010).

Oldhoff JM et al., Anti-IL-5 recombinant humanized monoclonal antibody (mepolizumab) for the treatment of atopic dermatitis, Allergy; 60(5):693-6, (2005).

Amini-Vaughan ZJ et al., Therapeutic strategies for harnessing human eosinophils in allergic inflammation, hypereosinophilic disorders, and cancer // Curr Allergy Asthma Rep. vol. 12, No. 5, p. 402-412, (2012).

Yong Sup Lee et al., in Studies on the site-selective N-acyliminium ion cyclazation: synthesis of (+)-glochidine and (+)-glochidiciine, Heterocycles, No. 1, vol. 37 (1994).

Weigand-Hilgetag, Eksperimentalnye metody v organichesko khimii, Experimental Methods in Organic Chemistry, ed. by N.N. Suvorov et al., pp. 445-446 and 451-452, (1968).

Shimotori et al., Asymmetric synthesis of d-lactones with lipase catalyst, Flavour and Fragrance Journal, V. 22, No. 6, p. 531-539, (2007).

Ito et al., Chemoselective Hydrogenation of Imides Catalyzed by CpRu (PN) Complexes and Its Application to the Asymmetric Synthesis of Paroxetine // Journal of the American Chemical Society, V. 129, No. 2, p. 290-291, (2007).

Polniaszek et al., Stereoselective nucleophilic additions to the carbon-nitrogen double bond. 3 Chiral acyliminium ions // Journal of Organic Chemistry, V. 55, No. 1, p. 215-223, (1990).

Methods of reducing eosinophil levels document—http://www.patengenius.com/patent/8501176.html.

Assa'Ad AH, et al., An Antibody against IL-5 reduces numbers of esophageal intraepithelial eosinophils in children with eosinophilic esophagitis. Gastroenterology. 141(5):1593-604, (2011).

Ainhoa Ardeo et al., A pratical approach to the fused β-carboline system. Asymmetric synthesis of indolo[2,3-a] indolizidinones via a diastereoselective intramolecular a-amidoalkylation reaction. /Tetrahedron Letters, 44, 8445-8448, (2003).

Kay AB et al., A role for eosinophils in airway remodeling in asthma/Trends Immunol. vol. 25, p. 477-82, (2004).

International Search Report—International Application No. PCT/RU2014/000855 dated Mar. 26, 2015.

PHARMACEUTICAL COMPOSITION COMPRISING GLUTARIMIDE DERIVATIVES AND USE THEREOF IN THE TREATMENT OF EOSINOPHILIC DISEASES

CROSS-REFERENCE TO RELATED APPLICATIONS

This application is a continuation of U.S. application Ser. No. 15/036,603, now pending, which is a U.S. National Stage application under 35 U.S.C. § 371 of International Application PCT/RU2014/000855 (published as WO 2015/072893 A1), filed Nov. 12, 2014, which claims priority to Application RU 2013150861, filed Nov. 14, 2013. Benefit of the filing date of each of these prior applications is hereby claimed. Each of these prior applications is hereby incorporated by reference in its entirety.

FIELD OF THE INVENTION

The invention relates to the use of biologically active glutarimide derivatives or pharmaceutically acceptable salts thereof as agents for the treatment of eosinophilic diseases.

BACKGROUND

Eosinophils are cells of the innate immunity. They are produced in the bone marrow and preferably circulate in the blood. The main effector function of eosinophils is an immediate release of cytoplasmic granules in response to activation by various stimuli. Cytoplasmic granules comprise pro-inflammatory mediators: cytokines, chemokines, lipid- and neuromediators, growth factors, and cationic proteins. The cationic proteins of eosinophils include 4 classes: major basic protein (MBP), eosinophil peroxidase (EPO), eosinophil cationic protein (ECP), and eosinophil-derived neurotoxin (EDN). In combination, these proteins have a cytotoxic action on both infectious microorganisms and tissues of a host, causing eosinophilic inflammation [Hogan S P, Rosenberg H F, Moqbel R, et al. Eosinophils: biological properties and role in health and disease//Clin Exp Allergy. 2008; 38(5):709-50]. The eosinophil count in the blood is normally 0.02-0.3 $10^9$/L, or 0.5 to 5% of the total leukocytes. An increased blood eosinophil count relative to the normal level is eosinophilia. Hypereosinophilia or large eosinophilia is a condition when the content of eosinophils in the blood is 15% or more, usually when the total leukocyte count is increased [Hoffman R, Benz Jr. E J, Shattil S J, et al., eds. Hematology: Basic Principles and Practice. 4th ed. Philadelphia, Pa.: Churchill Livingston; 2005: 768].

An increased level of eosinophils in the blood and tissues accompanies diseases of various etiology and pathogenesis. They include parasitic invasions, a broad spectrum of allergic diseases, such as asthma, rhinitis, nasal polyps, eosinophilic colitis, eosinophilic syndrome, allergic conjunctivitis, and atopic dermatitis; rheumatic diseases (rheumatoid arthritis, diffuse eosinophilic fasciitis, Churg-Strauss syndrome, nodular periarteritis); and pathologies of unclear etiology (eosinophilic esophagitis, eosinophilic gastroenteritis) [Blanchard C, Rothenberg M E. Biology of the eosinophil// Adv Immunol. 2009; 101:81-121].

Among allergic diseases, bronchial asthma, which is a chronic inflammatory airway disease that is characterized by episodic airflow obstruction, inflammation of the respiratory tract, and by an increased bronchial reactivity to non-specific allergens, is medically most important.

There are a lot of evidences that eosinophils are a key component of an allergic response in asthma. IL-3 and IL-5 secreted by mast cells provide the accumulation of eosinophils in lungs, followed by activation of these cells, which is accompanied by the release of LTC4, eosinophil cationic protein, major basic protein, neurotoxin, eosinophil peroxidase (EPO), transforming growth factor, and free radicals [Blanchard C, Rothenberg M E. Biology of the eosinophil// Adv Immunol. 2009; 101:81-121].

The activity of the inflammatory process in asthma has been found to be in direct correlation with the serum level of eosinophil cationic protein [Bjornsson E., Janson C., Hakansson L. et al. Serum eosinophil cationic protein in relation to bronchial asthma in young Swedish population. Allergy 1994; Vol. 49: 400-407]. Lavage fluid of patients with bronchial asthma has an increased eosinophil count. The eosinophil cell surface has low-affinity receptors for IgE and due to that eosinophils may be directly activated by cause-significant allergens. The eosinophil cell surface has further been found to have receptors for IL-2, IL-3, IL-5, GM-CSF, PAF, and prostaglandins. Through these receptors, the above-mentioned cytokines and lipid mediators are able to induce the activation of eosinphils that release mediators (LTC4, PAF) and cytokines (IL-3, IL-4, IL-5, IL-8, GM-CSF, TGFβ). Destruction of the airway epithelium, which results from the action of eosinophil proteins, causes the development of bronchial hyperreactivity and a reduction in the barrier function of the airway epithelium.

Now, a great attention is being attached to the role of eosinophils in the regeneration and remodulation of tissues because of a clear relationship that have been found to exist between eosinophilia in tissues and some fibrous diseases (endomyocardial fibrosis complicated with hepatic fibrosis in patients with hypereosinophilic syndrome, nodular sclerosing Hodgkin's disease, and subepithelial fibrosis in bronchial asthma) [Noguchi H. et al. Tissue eosinophilia and eosinophil degranulation in syndromes associated with fibrosis// Am. J. Pathol. 1992, Vol. 140. P. 521-528].

Eosinophils are a source of a number of fibrogenic and growth factors, including transforming growth factor-β (TGF-β) fibroblast growth factor (FGF)-2, vascular endothelial growth factor (VEGF), matrix metalloproteinase (MMP)-9, IL-1β, IL-13, and IL-17. Clinical trials involving anti-IL-5 antibodies also supported the role of eosinophils in the events associated with the deposition of specific matrix proteins in the reticular basement membrane [Kay A B, Phipps S, Robinson D S. A role for eosinophils in airway remodeling in asthma//Trends Immunol. 2004, Vol. 25, P. 477-82].

Today, the most common method for treating asthma is the use of corticosteroids (budesonide, beclomethasone dipropionate, fluticasone propionate, mometasone furoate) by inhalation. However, corticosteroids function by inducing a general immunosuppressive action, and there are adverse side effects caused by long-term administration thereof, such as high blood pressure, osteoporosis, and cataract development [Barnes P J. New drugs for asthma// Semin Respir Crit Care Med. 2012; 33(6):685-94]. Corticosteroids should be administered every day, and patient's compliance with this requirement is therefore another problem for the successful use of said therapeutic agents. In addition, there are corticosteroid-insensitive patients who need an alternative therapy. Selective targeting to eosinophils may overcome the side effects caused by the use of systemic immunosuppressive agents with pleiotropic action.

The drugs for reducing eosinophilia by inhibiting the interaction between interleukin-5 and receptor IL-5Rα on the eosinophil cell surface are currently in clinical trials. Such drugs include humanized monoclonal anti-IL-5 antibodies (mAt) and concurrent IL-5Rα inhibitors.

Among IL-5 neutralizing monoclonal antibodies, SB240563 (mepolizumab, Glaxo Smith Kline) is most effective. There are reports [Nair P, Pizzichini M M M, Kjarsgaard M, et al. Mepolizumab for prednisone-dependent asthma with sputum eosinophilia. NEJM. 2009; 360:985-93] that mepolizumab therapy of patients with prednisolone-dependent asthma reduces eosinophilia in the blood and sputum and, most importantly, improves patient's quality by reducing exacerbation frequency and a prednisolone dose. Another clinical trial showed that the administration of anti-IL-5 antibodies (mepolizumab) to the patients with corticosteroid-insensitive asthma also led to a reduction in exacerbation frequency and improved patient's quality according to the AQLQ (Asthma Quality of Life Questionnaire). In addition to the action on asthma, this trial also showed a therapeutic effect against polypous rhinosinusopathy [Haldar P, Brightling C E, Hargadon B, et al. Mepolizumab and exacerbations of refractory eosinophilic asthma. NEJM. 2009; 360:973-84].

In an independent clinical trial in adults with polypous rhinosinusopathy, mepolizumab significantly reduced the levels of ECP and a soluble form of IL-5Rα in the blood, and the concentration of IL-5Rα, IL-6, and IL-1b in the nose, which correlated with an alleviation of the disease, according to the total polyp score [Gevaert P, Van Bruaene N, Cattaert T, et al. Mepolizumab, a humanized anti-IL-5 mAb, as a treatment option for severe nasal polyposis. J Allergy Clin Immunol. 2011; 128(5):989-995].

The use of anti-IL-5 antibodies is not limited to bronchial asthma and polypous rhinosinusopathy. This therapy is also effective in other eosinophil-mediated diseases. For example, in patients with hypereosinophilic syndrome, mepolizumab therapy reduced eosinophilia in the blood and made it possible to reduce the administered dose of prednisolone [Rothenberg M E, Klion A D, Roufosse F E, et al. Treatment of patients with the hypereeosinophilic syndrome with mepolizumab. NEJM. 2008; 358(12):1215-28]. Patients with eosinophilic esophagitis treated with anti-IL-5 antibodies showed an improved clinical picture associated with a reduced dysphagia and a six-fold reduction in the blood eosinophil count, and in some patients, esophageal epithelial hyperplasia was reduced [Stein M L, Collins M H, Villanueva J M, et al. Anti-IL-5 (mepolizumab) therapy for eosinophilic esophagitis. J Allergy Clin Immunol. 2006; 118(6):1312-9]. Clinical trials of the drug in children showed that the patients having in the blood not more than 20 eosinophils in one field of microscope had improved symptoms, such as redness, fragility, and grooves and vertical lines on the esophageal mucosa [Assa'ad A H, Gupta S K, Collins M H, et al. An antibody against IL-5 reduces numbers of esophageal intraepithelial eosinophils in children with eosinophilic esophagitis. Gastroenterology. 2011; 141(5):1593-604].

Mepolizumab is also successfully used as therapy of eosinophilic vasculitis [Kahn J E, Grandpeix-Guyodo C, Marroun I, et al. Sustained response to mepolizumab in refractory Churg-Strauss syndrome. J Allergy Clin Immunol. 2010; 125:267-70]. In a 28-aged female, monthly administration of mepolizumab reduced the blood eosinophil count to normal, prevented the formation of corticosteroid asthma, and based on x-ray data, improved the condition of the lung parenchyma [Kim S, Marigowda G, Oren E, Israel E, Wechsler M. Mepolizumab as a steroid-sparing treatment option in patients with Churg-Strauss syndrome. J Allergy Clin Immunol. 2010; 125:1336-43]. In clinical trials in patients with eosinophilic vasculitis and pronounced eosinophilia, mepolizumab therapy made it possible to reduce the dose of corticosteroids. Eosinophilia also reduced, but after the trial completion, the exacerbation was repeated [Oldhoff J M, Darsow U, Werfel T, et al. Anti-IL-5 recombinant humanized monoclonal antibody (mepolizumab) for the treatment of atopic dermatitis. Allergy. 2005; 60(5):693-6].

Mepolizumab is reported [Amini-Vaughan Z J, Martinez-Moczygemba M, Huston D P. Therapeutic strategies for harnessing human eosinophils in allergic inflammation, hypereosinophilic disorders, and cancer //Curr Allergy Asthma Rep. 2012, Vol. 12, No 5. P. 402-412] hat to be in the second phase of clinical trials of therapy for asthma, eosinophilic esophagitis in adults, eosinophilic esophagitis in children, eosinophilic vasculitis, and polypous rhinosinusopathies, and in the third phase of clinical trials as a treatment of hypereosinophilic syndrome, eosinophilic esophagitis in children, rhinovirus-induced asthma, and chronic obstructive bronchitis. Another medicament, reslizumab (Cephalon), which is also a humanized monoclonal anti IL-5 antibody SCH55700, is in the second phase of clinical trials as a therapy for hypereosinophilic syndrome and loiasis, and in the third phase as a therapy of asthma and eosinophilic esophagitis in children. All these allow for concluding that selective therapy aimed at reducing eosinophilia is a perspective approach to the treatment of diseases mediated by this cell type (bronchial asthma, allergic rhinitis, allergic conjunctivitis, atopic dermatitis, polypous rhinosinusopathy, eosinophilic esophagitis, eosinophilic vasculitis, and hypereosinophilic syndrome).

However, mAt therapy has several drawbacks. Monoclonal antibodies are expensive therapeutic agents that should be administered for a month or two. An important factor is a problem of patient's non-compliance with physician's order, which is because of multiple visits to a physician's office to receive the drug injections. In addition, allotype divergence between a patient and a therapeutic antibody can lead to that the monoclonal antibody-based therapy becomes ineffective. A high dose of mAt and a possibility of forming immune complexes also may reduce the efficiency of passive immunization.

Other methods providing therapeutic agents against pathological conditions characterized by eosinophilia are disclosed in WO 97/45448 and WO 03/040164. Application WO 97/45448 provides the use of "modified and variant forms of IL5 molecules capable of antagonizing or reducing, in another way, the activity of IL-5" to improve, alleviate, or reduce effects deviated from the norm, which are caused by native and mutant forms of IL5. It is reported that the antagonizing action is a result of variant forms of IL5 that bind with the low-affinity chain of IL5R but not with high-affinity receptors. Acting in such a way, the variants compete with IL5 for binding with its receptors without any effect on the physiological action of IL5.

Application WO 03/040164 provides a composition for vaccination directed to endogenous formation of antibodies to IL-5, IL-13, and eotoxin, i.e. to key factors of maturation, activation, localization, and vitality of eosinophils. The composition comprises a virus-like particle and at least one protein or peptide of IL-5, IL-13 and/or eotaxin bound thereto. According to the invention, said composition is useful in the production of vaccines for the treatment of allergic diseases with an eosinophilic component and as a pharmaccine to prevent or cure allergic diseases with an eosinophilic component.

Application Ser. No. 8501176 provides the use of antibodies binding to IL-5R. These antibodies comprise a binding site recognizing IL-5 receptors (IL-5R) and Fc-fragment. The claimed method reduces the eosinophil count in the blood, marrowbone, gastro-intestinal tract (for example, esophagus, stomach, small intestine and large gut), or lungs, thereby reducing clinical manifestations of asthma and chronic obstructive bronchitis of lungs in human beings (http://www.patentgenius.com/patent/8501176.html).

Yong Sup Lee et al. in Studies on the site-selective N-acyliminium ion cyclazation: synthesis of (±)-glochidine and (±)-glochidicine, Heterocycles, Vol 37, No 1. 1994, disclose the preparation of histamine succinimide by fusing histamine dihydrochloride together with succinic anhydride under heating the initial reagents to 200-230° C. for 40 minutes.

The publication of international application WO 2007/007054 discloses succinimide and glutarimide derivatives of general formula (I), having inhibitory action on DNA methylation in cells, in particular tumor cells. Compounds disclosed in said publication are prepared by an addition reaction between an amino derivative comprising a hydrocarbon chain and a corresponding anhydride or acid, or ester, followed by optional cyclization, if necessary in the presence of a base.

The described methods of synthesis imides of glutaric acid comprise heating a dicarboxylic acid or a derivative thereof, such as anhydride, diester, etc., with a primary amine or amide thereof (thermal cyclization) [Weigand-Hilgetag, Eksperimentalnye metody v organicheskoi khimii [Experimental Methods in Organic Chemistry], ed. by N. N. Suvorov, M., Khimiya, 1968; p. 446], cyclization of monoamides of corresponding dicarboxylic acids by using a dehydrating agent as a carboxylic group-activating reagent, such as acetic anhydride [Shimotori et al, Asymmetric synthesis of δ-lactones with lipase catalyst. Flavour and Fragrance Journal, 2007, V. 22, No. 6, P. 531-539], acetyl chloride [Ito et al., Chemoselective Hydrogenation of Imides Catalyzed by CpRu(PN) Complexes and Its Application to the Asymmetric Synthesis of Paroxetine.//Journal of the American Chemical Society, 2007, V. 129, No. 2, P. 290-291], carbonyldiimidazole [Polniaszek, et al., Stereoselective nucleophilic additions to the carbon-nitrogen double bond. 3. Chiral acyliminium ions.//Journal of Organic Chemistry, 1990, V. 55, No. 1, P. 215-223], glutaric or succinic anhydrides [Ainhoa Ardeo et al, A practical approach to the fused β-carboline system. Asymmetric synthesis of indolo[2,3-α]indolizidinones via a diastereoselective intramolecular α-amidoalkylation reaction. /Tetrahedron Letters, 2003, 44, 8445-8448].

The international publication of patent application WO2007/000246 provides a method of synthesis of glutarimides by alkylation of piperidine-2,6-dione and pyrrolidin-2,5-dione with corresponding halo derivatives in DMF, followed by separating the target substituted imide derivatives by preparative chromatography, which is not applicable for the synthesis of macro amounts.

Thus, the object of the present invention is the use of non-toxic glutarimide derivatives effective for the treatment of eosinophilic diseases, preferably of allergic nature, such as bronchial asthma, allergic rhinitis, polypous rhinosinusopathies, eosinophilic colitis, eosinophilic syndrome, allergic conjunctivitis, atopic dermatitis, Churg-Strauss syndrome, anaphylactic shock, Quincke's edema, eosinophilic vasculitis, eosinophilic esophagitis, eosinophilic gastroenteritis, and fibroses.

SUMMARY OF THE INVENTION

The present invention relates to use of glutarimide derivatives of general formula (I):

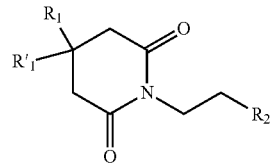

wherein $R_1$ and $R'_1$ are independently hydrogen or $C_1$-$C_6$alkyl, for example, methyl;

$R_2$ is

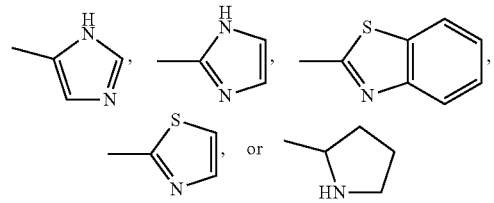

optionally substituted with $C_1$-$C_6$alkyl, for the treatment of eosinophilic diseases, preferably of allergic nature, such as bronchial asthma, allergic rhinitis, polypous rhinosinusopathies, eosinophilic colitis, eosinophilic syndrome, allergic conjunctivitis, atopic dermatitis, Churg-Strauss syndrome, anaphylactic shock, Quincke's edema, eosinophilic vasculitis, eosinophilic esophagitis, eosinophilic gastroenteritis, and fibroses, as disclosed in application RU 2013116826 of Dec. 4, 2013.

The inventors have found that glutarimide derivatives suppress eosinophilia in various inflammation models in all tested media (blood, bronchoalveolar lavage (BAL), and tissues). In particular, in the model of sephadex-induced lung inflammation in rats, glutarimide derivatives reduced the eosinophil count in BAL, and in the model of ovalbumin-induced asthma in guinea pigs, glutarimide derivatives reduced eosinophilia in BAL and blood.

Thus, the present invention relates to a therapeutic method for treating eosinophilic diseases, preferably of allergic nature, such as bronchial asthma, allergic rhinitis, polypous rhinosinusopathies, eosinophilic colitis, eosinophilic syndrome, allergic conjunctivitis, atopic dermatitis, Churg-Strauss syndrome, anaphylactic shock, Quincke's edema, eosinophilic vasculitis, eosinophilic esophagitis, eosinophilic gastroenteritis, and fibroses, the method comprising administering to a patient an effective amount of a glutarimide derivative of general formula (I) or a pharmaceutically acceptable salt thereof.

The present invention also relates to a therapeutic agent for the treatment of eosinophilic diseases, preferably of allergic nature, such as bronchial asthma, allergic rhinitis, polypous rhinosinusopathies, eosinophilic colitis, eosinophilic syndrom, allergic conjunctivitis, atopic dermatitis, Churg-Strauss syndrome, anaphylactic shock, Quincke's edema, eosinophilic vasculitis, eosinophilic esophagitis, eosinophilic gastroenteritis, and fibrosis, wherein the therapeutic agent is a glutarimide derivative of general formula (I) or a pharmaceutically acceptable salt thereof.

Another subject matter of the present invention is a pharmaceutical composition for the treatment of eosinophilic diseases, preferably of allergic nature, such as bronchial asthma, allergic rhinitis, polypous rhinosinusopathies, eosinophilic colitis, eosinophylic syndrome, allergic conjunctivitis, atopic dermatitis, Churg-Strauss syndrome, anaphylactic shock, Quincke's edema, eosinophilic vasculitis, eosinophilic esophagitis, eosinophilic gastroenteritis, and fibrosis, the composition comprising an effective amount of a glutarimide derivative of general formula (I) or a pharmaceutically acceptable salt thereof, and a pharmaceutically acceptable carrier.

The synthesis of the above-mentioned glutarimide derivative of general formula (I) is disclosed in application RU 2013116826 of Dec. 4, 2013.

Compound used in the present invention may be prepared by a method comprising heating of initial dicarboxylic acid monoamides with a dehydrating agent in an organic solvent or in the dehydrating agent as such, optionally adding sodium acetate. The dehydrating agent used in the method may include dicarboxylic acid anhydrides, organic acid chloroanhydrides, and carbonyldiimidazole.

Initial dicarboxylic acid monoamides and methods for preparing thereof are disclosed in the publication of international application WO 1999/001103.

DETAILED DESCRIPTION OF THE INVENTION

Preferred compounds used in the present invention are compounds of general formula (I)

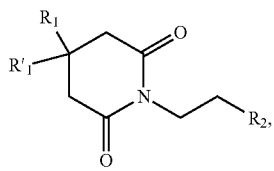

wherein $R_1$ and $R'_1$ are independently hydrogen or methyl;
$R_2$ is

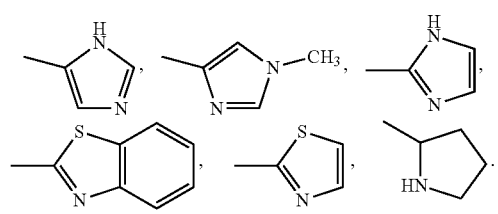

The most preferred compounds of the present invention are compounds presented in Table 1.

TABLE 1

| The number of compound | Structure |
|---|---|
| 1 |  |
| 2 | 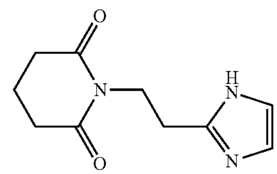 |
| 3 | 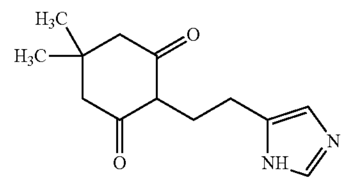 [SMILES: CC1(C)CC(=O)C(CCc2cnc[nH]2)C(=O)C1] |
| 4 | 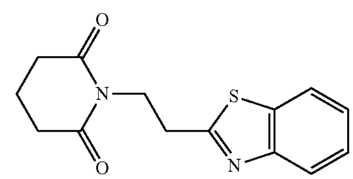 [SMILES: O=C1CCCC(=O)N1CCc1nc2ccccc2s1] |
| 5 | 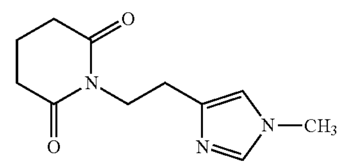 [SMILES: Cn1cnc(CCN2C(=O)CCCC2=O)c1] |
| 6 | 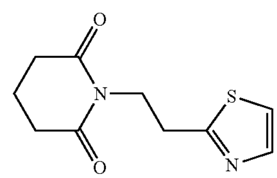 [SMILES: O=C1CCCC(=O)N1CCc1nccs1] |
| 7 | 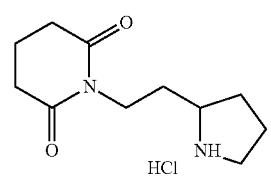 [SMILES: O=C1CCCC(=O)N1CCC1CCCN1 ; Cl] |
| 8 | 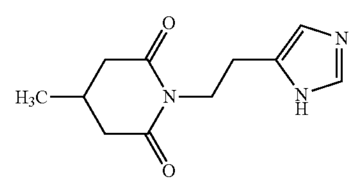 [SMILES: CC1CC(=O)N(CCc2cnc[nH]2)C(=O)C1] |

The pharmaceutically acceptable salts of the compounds according to the present invention may include additive salts of organic acids (for example, formiate, acetate, maleate, tartrate, methanesulfonate, benzenesulfonate, toluenesulfonate, etc.), additive salts of inorganic acids (for example, hydrochloride, hydrobromide, sulphate, phosphate, etc.), and salts with amino acids (for example, an asparaginic acid salt, a glutamic acid salt, etc.), preferably chlorohydrates and acetates.

Glutarimide derivatives of general formula (I) are therapeutically active against eosinophilic diseases.

The compounds of the present invention may be used, in particular, for the treatment of bronchial asthma, allergic rhinitis, polypous rhinosinusopathies, eosinophilic colitis, eosinophilic syndrome, allergic conjunctivitis, atopic dermatitis, Churg-Strauss syndrome, anaphylactic shock, Quincke's edema, eosinophilic vasculitis, eosinophilic esophagitis, eosinophilic gastroenteritis, and fibroses.

The compounds according to the present invention are administered in an effective amount that provides a desired therapeutic effect.

The compounds of general formula (I) may be administered orally, topically, parenterally, intranasally, by inhalation, and rectally in a unit dosage form comprising a non-toxic pharmaceutically acceptable carrier.

The term "parenteral administration" as used herein means subcutaneous, intravenous, intramuscular injection, or infusion.

The compounds according to the present invention may be administered to a patient at a dose of from 0.1 to 30 mg/kg of body weight once daily, preferably at a dose of from 0.25 to 10 mg/kg one or more times a day.

In addition, it should be noted that a particular dose for a particular patient depends on many factors, including the activity of a used compound, patient's age, body weight, gender, general health condition, diet, and also on the time and route of administration of a therapeutic agent, the rate of its excretion from the body, a particularly used combination of therapeutic agents, and the disease severity in an individual to be treated.

The pharmaceutical composition according to the present invention comprises a compound of general formula (I) in an amount effective to achieve a desired technical result, and may be administered in a unite dosage form (for example, solid, semi-solid, or liquid form) comprising the compound according to the present invention as an active ingredient in a mixture with a carrier or an excipient suitable for intramuscular, intravenous, oral, sublingual, inhalation, intranasal, and intrarectal administration. In the composition, the active ingredient may be in combination with conventional nontoxic pharmaceutically acceptable carriers suitable for the manufacture of solutions, tablets, pills, capsules, dragee, suppositories, emulsions, suspensions, ointments, gels, and any other dosage forms.

The compounds that can be used as an excipient are various compounds, such as saccharides, for example, glucose, lactose, or sucrose, mannitol, or sorbitol, cellulose derivatives, and/or calcium phosphate, for example, tricalcium phosphate or acidic calcium phosphate. The compounds that can be used as a binder, tare compounds such as starch paste, for example, corn, wheat, rice, and potato starch, gelatin, tragacanth, methylcellulose, hydroxypropyl methylcellulose, carboxymethylcellulose, and/or polyvinylpyrrolidone. If necessary, there may be used a disintegrating agent, such as the aforementioned starches and carboxymethyl starch, crosslinked polyvinylpyrrolidone, agar, or alginic acid or a salt thereof, such as sodium alginate.

Additives that may be optionally used include flowability-control agents and lubricants, such as silicon dioxide, talc, stearic acid and salts thereof, such as magnesium stearate or calcium stearate, and/or propylene glycol.

The core of a coted pill is usually coated with a layer that is resistant to gastric acid. A concentrated solution of saccharides that may optionally comprise gum arabic, talc, polyvinylpyrrolidone, polyethylene glycol, and/or titanium dioxide, and suitable organic solvents or salts thereof may be used for this purpose.

Additives may also include stabilizers, thickening agents, colorants, and fragrances.

As an ointment base, there may be used hydrocarbon ointment bases, such as white Vaseline and yellow Vaseline (Vaselinum album and Vaselinum flavum), Vaseline oil (Oleum Vaselini), and white ointment and liquid ointment (Unguentum album and Unguentum flavum), and the substances, such as solid paraffin or wax, can be used as an additive providing a firmer texture; absorptive ointment bases, such as hydrophilic Vaseline (Vaselinum hydrophylicum), lanoline (Lanolinum), and cold cream (Unguentum leniens); water-removable ointment bases, such as hydrophilic ointment (Unguentum hydrophylum); water-soluble ointment bases, such as polyethylene glycol ointment (Unguentum Glycolis Polyaethyleni); bentonite bases; and others.

Methylcellulose, carboxymethylcellulose sodium salt, oxypropylcellulose, polyethylene glycol, polyethylene oxide, or carbopol may be used as a base for gels.

Bases for suppositories may be water-insoluble bases, such as cocoa butter; water-soluble or water-miscible bases, such as gelatin-glycerol or polyethylene oxide bases; or combined bases, such as soap-glycerol bases.

When preparing a unit dosage form, the amount of an active agent used in combination with a carrier may vary depending on a recipient under the treatment and on a particular method of administration of the therapeutic agent.

For example, when the compounds according to the present invention are used in the form of a solution for injections, the amount of the active agent in this solution is up to 5 wt. %. A diluent may be a 0.9% sodium chloride solution, distilled water, a Novocain solution for injection, Ringer's solution, a glucose solution, or a specific solubilizing adjuvant. When the compounds according to the present invention are administered in the form of a tablet or suppository, their amount is up to 200 mg per unit dosage form.

Dosage forms according to the present invention are prepared by conventional procedures, such as blending, granulation, formation of a coating pill, dissolution, and lyophilization.

It should be noted that the compounds according to the present invention have no side effects and contraindications for administration. In addition, fatal cases in the experimental animals were not registered in toxicity tests of the compounds according to the present invention, administered orally at a dose of 1500 mg/kg.

The detailed description of the compounds according to the present invention, and studies of their pharmacological activity are disclosed in the following examples that are intended for purposes of illustration only and are not intended to limit the scope of the invention.

EXPERIMENTAL PART

The synthesis of the above-mentioned glutarimide derivative of general formula (I) is disclosed in application RU 2013116826 of Dec. 4, 2013.

Examples of the Synthesis of Glutarimide Derivatives of General Formula (I)

Materials and Methods

The identity of the obtained compounds were assessed by the thin-layer chromatography (TLC) method on plates "Kieselgel 60 F254" ("Merck", German) in a solvent system: chloroform-methanol (9:1) (1), chloroform-methanol (1:1) (2).

Chromatograms and electrophoregrams were stained with a chlorotetramethylbenzene reagent and Pauly's reagent.

LC/MS system for analysis of multicomponent mixtures Shimadzu Analytical HPLC SCL10Avp; mass spectrometer PE SCIEX API 165 (150) (Canada). Conditions: column: Waters ACQUITY UPLC BEH C18 2.1×50 mm 1.7 µm, gradient elution system: water with 0.1% HCOOH - acetonitrile with 0.1% HCOOH.

Analytical-scale reversed phase HPLC was performed on a Shimadzu HPLC chromatograph under the following conditions: column: Luna C18(2) 100 A, 250×4.6 mm (Serial number 599779-23), gradient elution system: a phosphate buffer solution (pH 3.0):methanol (condition A); column: Merk.LiChroCART 250×4 mm 5 µm LiChrospher 100RP-8E 5 µmC8 (Serial number 1.50837.0001), gradient elution system: an ammonium acetate buffer solution (pH 7.5): acetonitrile (condition B); gradient elution system: a buffer containing 0.0025M sodium 1-hexylsulphonate (pH 3):acetonitrile (condition C); and column: Symmetry C18 150×4.6 mm, gradient elution system: a buffer solution containing 0.0025M sodium 1-hexylsulphonate (pH 3):acetonitrile (condition D).

$^1$H NMR spectra were registered on a spectrometer (Bruker DPX-400, German).

High-resolution mass-spectra were obtained on a time-of-flight mass spectrometer by a method of matrix-assisted laser-desorption ionization with 2,5-dihydroxybensoic acid used as a matrix, on an Ultraflex mass spectrometer ("Bruker", German).

Example 1

1-(2-(1H-imidazol-4-yl)ethyl)piperidine-2,6-dione (compound 1)

N,N'-dimethylformamide (60 mL) and 2-(imidazol-4-yl)-ethanamide of pentandioic-1,5 acid (20 g) were filled in a 250 mL flat-bottom flask. Carbonyldiimidazole (17.3 g; 1.2 equiv.) was added under vigorous stirring. The reaction mixture was heated under stirring to 90° C. for 2 hours. The reaction was controlled by $^1$H-NMR spectroscopy (a sample (0.5 mL) was diluted with a sulphuric ether, and the precipitate was dissolved in DMSO-$d_6$). When the initial 2-(imidazol-4-yl)-ethanamide of pentandioic-1,5 acid was absent in the reaction mass, the mass was cooled and poured out into a three-fold volume of methyl tert-butyl ether (180 mL). The reaction mixture was allowed to stand for 1 hour, and the precipitate was filtered, washed with 60 mL of methyl tert-butyl ether, and dried. The yield of the crude 1-(2-(1H-imidazol-4-yl)ethyl)piperidine-2,6-dione was 12.4 g (67%).

The crude 1-(2-(1H-imidazol-4-yl)ethyl)piperidine-2,6-dione (12 g) and isopropanol (36 mg) were filled in a 100 mL flat-bottom flask. The mixture was heated to complete dissolution of the residue, then 1.2 g of activated carbon were added thereto, and the mixture was aged at boiling temperature for an hour. The solution being hot was filtered through a pre-heated ceramic filter. The residue on the filter was washed with 6 mL of hot isopropanol. The hot stock solution was cooled to room temperature and allowed to stand for crystallization over night under stirring. Precipitated crystals were filtered, washed with mL of cool isopropanol, and dried. After recrystallization, the amount of the obtained 1-(2-(1H-imidazol-4-yl)ethyl)piperidine-2,6-dione was 10.1 g (84%). Rf 0.43 (1). The product was analyzed with an LC/MS method: an individual peak at a retention time of 1.57 min; [M+H]$^+$=208. HPLC under condition A: an individual peak at a retention time of 15.5 min. $^1$H NMR (400.13 MHz, DMSO-$d_6$, δ, m.d., J/Hz): 1.81 (quint, 2H, CH$_2$CH$_2$CH$_2$, J=6.5 Hz), 2.58 (m, 6H, CH$_2$C, CH$_2$CH$_2$CH$_2$); 3.82 (t, 2H, CH$_2$N, J=7.8 Hz), 6.77 (br.s, 2H, CCH), 7.49 (s, 1H, NCHN), 11.81 (br.s, 1H, NH).

If necessary, in the synthesis of the compounds according to the present invention, the nitrogen atom in heterocycles may be protected by using, for example, a carbamate protecting group, such as tert-butoxycarbonyl group (Boc).

The compounds presented in Table 2 were obtained according to the above-indicated method.

TABLE 2

| The number of a compound | Structural formula | Physical and chemical data |
|---|---|---|
| 2 | (piperidine-2,6-dione with ethyl-imidazole substituent) | LC/MS: an individual peak at a retention time of 0.41 min, [M + H]$^+$ = 208. HPLC under condition B: an individual peak at a retention time of 16.72 min. $^1$H-NMR (400.13 MHz, DMSO-$d_6$, δ, m.d., J/Hz): 1.82 (quint, 2H, CH$_2$CH$_2$CH$_2$, J = 6.5 Hz); 2.57 (t, 4H, CH$_2$CH$_2$CH$_2$, J = 6.5 Hz); 2.72 (t, 2H, CH$_2$C, J = 7.5 Hz); 3.90 (t, 2H, CH$_2$N, J = 7.5 Hz); 6.86 (s, 2H, CH$_2$N, J = 7.5 Hz); 11.72 (br.s, 1H, NH) |
| 3 | (4,4-dimethyl-piperidine-2,6-dione with ethyl-imidazole substituent) | LC/MS: an individual peak at a retention time of 0.41 min, [M + H]$^+$ = 236. HPLC under condition A: an individual peak at a retention time of 22.16 min. $^1$H-NMR (400.13 MHz, DMSO-$d_6$, δ, m.d., J/Hz): 0.91 (s, 6H, CH$_3$); 2.58 (m, 6H, CH$_2$C, CH$_2$CCH$_2$); 3.86 (t, 2H, CH$_2$N, J = 7.3 Hz); 6.60, 6.85 (br.s, 1H, CCH); 7.50 (br.s, 1H, NCHN); 11.8 (br.s, |

TABLE 2-continued

| The number of a compound | Structural formula | Physical and chemical data |
|---|---|---|
| | | 1H, NH) |
| 7 | (piperidine-2,6-dione N-linked to CH₂CH₂-pyrrolidine, HCl salt) | LC/MS: an individual peak at a retention time of 0.74 min, [M + H]⁺ = 211. HPLC under condition C, an individual peak at a retention time of 10.8 min. ¹H-NMR (400.13 MHz, DMSO-d₆, δ, m.d., J/Hz): 1.52 (m, 1H, pyrrolidine), 1.72 (m, 1H, pyrrolidine), 1.86 (m, 5H, pyrrolidine + C$\underline{H}_2$CH + COCH₂CH₂CH₂CO), 2.10 (m, 1H, pyrrolidin$\overline{e}$), 2.61 (t, 4H, COCH₂CH₂CH₂CO, J = 6.4 Hz), 3.10 (m, 2$\overline{H}$, pyrrolidine), 3.30 (m, 1H, pyrrolidine), 3.68 (m, 2H, C$\underline{H}_2$N), 8.93 (s, 1H, NH) |
| 8 | (4-methyl-piperidine-2,6-dione N-linked to CH₂CH₂-imidazole) | LC/MS: an individual peak at a retention time of 1.9 min, [M + H]⁺ = 222. HPLC under condition C, an individual peak at a retention time of 13.8 min. ¹H-NMR (400.13 MHz, DMSO-d₆, δ, m.d., J/Hz): 0.95 (d, 3H, CH₃, J = 6.5 Hz), 2.15 (m, 1H, COCH₂C$\underline{H}$CH₂CO); 2.35 (m, 2H, C$\underline{H}_2$C); 2.62 (m, 4H, COC$\underline{H}_2$CHC$\underline{H}_2$CO), 3.82 (t, 2H, CH₂N, J = 7.8 Hz), 6.80 (s, 1H, CC$\underline{H}$), 7.56 (s, 1H, NC$\underline{H}$N) |

Example 2

1-(2-(1,3-benzothiazol-2-yl)ethyl)piperidine-2,6-dione (compound 4)

A mixture of 2-(1,3-benzothiazol-2-yl)ethanamide of pentandioic-1,5 acid (22 g; 0.075 mol) and acetic anhydride (23 g; 0.225 mol) were boiled in 150 mL of dioxane for 3 hours. The dioxane was removed under vacuum, 200 mL of water was added, and the mixture was neutralized with 30% sodium hydroxide to neutral pH. The precipitated oil was triturated until crystals formed. The precipitate was purified by chromatography (SiCO₂ 60-100 μm, eluent: ethyl acetate-hexane (1:1). LC/MS, an individual peak at a retention time of 2.26 min [M+H]⁺=275. HPLC under condition A, individual peak at a retention time of 9.3 min. ¹H-NMR (400.13 MHz, DMSO-d₆, δ, m.d., J/Hz): 1.85 (quint, 2H, CH₂CH₂CH₂, J=6.8 Hz); 2.59 (t, 4H, CH₂CH₂CH₂, J=6.8 Hz); 3.24 (t, 2H, CH₂C, J=7.3 Hz); 4.08 (t, 2H, CH₂N, J=7.3 Hz); 7.43, 7.49 (t, 1H, Ar, J=7.6 Hz); 7.96, 8.04 (d, 1H, Ar, J=7.6 Hz).

The compounds presented in Table 2 were obtained according to the above-indicated method.

TABLE 3

| The number of a compound | Structural formula | Physical and chemical data |
|---|---|---|
| 5 | (piperidine-2,6-dione N-linked to CH₂CH₂-(N-methyl)imidazole) | LC/MS: an individual peak at a retention time of 0.21 min, [M + H]⁺ = 222. HPLC under condition B, an individual peak at a retention time of 20.7 min. ¹H-NMR (400.13 MHz, DMSO-d₆, δ, m.d., J/Hz): 1.82 (quint, 2H, CH₂CH₂CH₂, J = 6.4 Hz), 2.53 (m, 2H, CH₂C), 2.58 (t, 4H, CH₂CH₂CH₂, J = 6.4 Hz), 3.57 (s, 3H, NMe), 3.80 (t, 2H, CH₂N, J = 7.8 Hz), 6.85 (s, 1H, CCH), 7.42 (s, 1H, NCHN) |

TABLE 3-continued

| The number of a compound | Structural formula | Physical and chemical data |
|---|---|---|
| 6 | 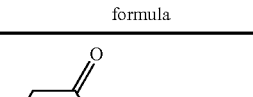 | LC/MS: an individual peak at a retention time of 1.43 min, [M + H] $^+$ = 225. HPLC under condition A, an individual peak at a retention time of 31.28 min. $^1$H-NMR (400.13 MHz, DMSO-$d_6$, δ, m.d., J/Hz): 1.82 (quint, 2H, $CH_2CH_2CH_2$, J = 6.5 Hz), 2.58 (t, 4H, $CH_2CH_2CH_2$, J = 6.5 Hz), 3.12 (t, 2H, $CH_2C$, J = 7.4 Hz), 3.97 (t, 2H, $CH_2N$, J = 7.4 Hz), 7.58 (d, 1H, SCH, J = 3.2 Hz), 7.70 (d, 1H, NCH, J = 3.2 Hz) |

Example 3

Coated tablets, 2 mg, 10 mg, and 100 mg

Composition of a Coated Tablet

| Ingredient | 2 mg | 10 mg | 100 mg |
|---|---|---|---|
| Active agent: | | | |
| Compound of general formula I | 2.00 mg | 10 mg | 100 mg |
| Additives: | | | |
| Microcrystalline cellulose | 47.70 mg | 70.55 mg | 95.90 mg |
| Lactose monohydrate | 49.00 mg | 67.50 mg | 99.00 mg |
| Sodium starch glycolate | 0.50 mg | 0.75 mg | 1.50 mg |
| Talc | 0.40 mg | 0.60 mg | 1.20 mg |
| Magnesium stearate | 0.40 mg | 0.60 mg | 2.40 mg |
| Tablet core weight | 100.00 mg | 150.00 mg | 300.00 mg |
| Film coating | 3.00 mg | 4.50 mg | 9.00 mg |
| Tablet weight | 103.00 mg | 154.50 mg | 309.00 mg |

Tests of Biological Activity
Materials and Methods

Morphological study of histologic preparations was performed using a light-optical microscope (Leica DM LS, Leica Microsystems, German). Micromorphometric analysis was performed using an ocular micrometer scale mounted in the microscope Leica DM LS. Photomicrographs were made with a digital photo camera (Leica DC 320).

Mathematical analysis of the obtained results was made using variation statistics methods with software Statistica 6.0. Data was analyzed with descriptive statistics: normal distribution of the data was verified according to Shapiro-Wilk test. As all data fitted normal distribution, the analysis of between-group variance was made by parametric methods, such as Student's t-test. Differences were considered significant if $p<0.05$.

An infinite number of examples provided below illustrate the biological activity of the claimed compounds of general formula (I).

Example 4

Evaluation of the Efficiency of the Compounds of General Formula (I) in a Guinea Pig Model of Asthma Bronchial asthma in guinea pigs was induced by a standard method [Ricciardolo F L, Nijkamp F, De Rose V, Folkerts G. The guinea pig as an animal model for asthma// Current Drug Targets. 2008 June; 9(6):452-65]. The animals were immunized by one parenteral administration of 0.5 mL of a solution comprising 100 μg/mL ovalbumin (Sigma) and 100 mg/mL aluminium hydroxide. Intact animals received a physiological saline solution in an amount of 0.5 mL.

On days 29, 30 and 31, hyperactivity of the respiratory airways was provoked by inhalation administration of ovalbumin in ascending concentrations of 0.1, 0.3, and 0.5 mg/mL on days 1, 2, and 3 of the provocation, respectively. The inhalation lasted 5 minutes or until asphyxia symptoms became apparent (fall to one side). On day 32, the animals received a challenging dose of ovalbumin (1 mg/mL) for 5 minutes, while assessing a bronchospastic reaction.

The studied compounds were administered to the animals once daily every day for 6 or 10 days; the administration was terminated two days before the administration of the challenging dose of antigen.

The bronchospastic reaction was assessed by a change in the rate and depth of the respiratory movements and by the asphyxia symptom such as fall to one side. Spirogram was registered by laboratory experimental equipment (ADInstruments, Australia), using a base recording station (PowerLab 8sp.) and software LabCart. The registration was made using airflow sensors for laboratory animals and a spirograph with an integrated amplifier (ADInstruments).

The bronchoalveolar lavage (BAL) and cardiac cavity blood were derived from the animals 24 hours after administration of the challenging dose. The BAL was collected under anesthesia by lavaging the lungs with 5 mL of a physiological saline solution heated to 37° C. through the trachea, using a syringe dosing device.

The absolute number of cell elements in 1 μL of the lavage (cytosis) was counted in the bronchoalveolar lavage, using the Goryaev camera. Then, the BAL was centrifuged at 200 g for 10 minutes. The residue was used to prepare swabs that were fixed in methanol and stained according to Romanovsky-Giemsa to count endopulmonary cytogram.

The blood was analyzed with a hemocytometer to determine leykoformula.

The study comprised 3 experiments, wherein the first one was directed to the evaluation of the effect of claimed compounds 1-6 on the cell composition of the BAL, the second and the third experiments were aimed at evaluating the effect of compounds 1 and 2 on the cell composition of the BAL, the cell composition of the blood, and on the bronchospasm severity.

Ten-time administration of compounds 1-6 to guinea pigs at a dose of 14 mg/kg reduced the level of cell elements in the BAL from $17.3 \times 10^9$ cells/L down to $2.5-6.3 \times 10^9$ cells/L (see Table 4). The studied compounds preferably resulted in a reduction of the eosinophil count: in the control group, the eosinophil count in the BAL was $7.05 \times 10^9$ cells/L, and in the group receiving the treatment, it was $0.60-1.61 \times 10^9$ cells/L, i.e. less by 91-77%.

TABLE 4

Content of cell elements in BAL in the model of bronchial asthma in guinea pigs
(M ± m, n = 9)

| Group | Dose of compound, mg/kg | Times of administration | Cytosis, $10^9/\pi$ | Eosinophils, $10^9/L$ | Neutrophils, $10^9/L$ | Monocytes, $10^9/L$ | Lymphocytes, $10^9/L$ |
|---|---|---|---|---|---|---|---|
| Intact | — | | 1.0 ± 0.1 | 0.07 ± 0.01 | 0.16 ± 0.03 | 0.30 ± 0.05 | 0.38 ± 0.04 |
| Control | — | | 17.3 ± 1.9* | 7.05 ± 0.68* | 1.78 ± 0.46 | 2.70 ± 0.59* | 4.92 ± 1.02* |
| Compound 1 | 14 | 10 | 2.5 ± 0.5& | 0.89 ± 0.23*& | 0.36 ± 0.09 | 0.35 ± 0.09* | 0.70 ± 0.13* |
| Compound 2 | | | 6.3 ± 1.1*& | 1.30 ± 0.29*& | 1.05 ± 0.16*& | 0.60 ± 0.14* | 1.53 ± 0.50* |
| Compound 3 | | | 2.9 ± 0.4*& | 0.93 ± 0.31*& | 0.36 ± 0.08 | 0.71 ± 0.18& | 0.72 ± 0.08* |
| Compound 4 | | | 3.5 ± 1.1*& | 1.25 ± 0.34*& | 0.43 ± 0.12 | 0.85 ± 0.19& | 0.81 ± 0.11* |
| Compound 5 | | | 5.9 ± 1.5*& | 1.61 ± 0.86*& | 1.05 ± 0.33 | 0.84 ± 0.23* | 1.35 ± 0.34* |
| Compound 6 | | | 4.9 ± 1.2*& | 0.60 ± 0.21*& | 0.97 ± 0.28* | 0.83 ± 0.18* | 1.03 ± 0.24* |

Note:
*difference from the intact group, according to Student's t-test, $p < 0.05$
&difference from the control group Student's t-test, $p < 0.05$ The administration of the studied compounds at lower doses (0.045, 0.14, and 1.4 mg/kg) and in two regimens (10 and 6 times) showed that the compounds reduced eosinophilia in BAL within a broad range of doses (0.045 to 14 mg/kg) and in various treatment schemes (see Table 5). In addition, the compounds reduced the lymphocyte count in all tested doses, and the monocyte count in the BAL was also reduced in some doses, which is indicative of the suppression of a local inflammatory reaction in the lung.

TABLE 5

Content of cell elements in BAL in the model of bronchial asthma in guinea pigs
(M ± m, n = 8)

| Group | Dose of compound, mg/kg | Times of administration | Cytosis, $10^9/L$ | Eosinophils, $10^9/L$ | Neutrophils, $10^9/L$ | Monocytes, $10^9/L$ | Lymphocytes, $10^9/L$ |
|---|---|---|---|---|---|---|---|
| Experiment No. 1 | | | | | | | |
| Intact | — | | 0.22 ± 0.01 | 0.02 ± 0.002 | 0.06 ± 0.003 | 0.06 ± 0.006 | 0.075 ± 0.008 |
| Control | — | | 19.3 ± 0.2* | 0.96 ± 0.17* | 0.18 ± 0.047* | 0.54 ± 0.06* | 0.24 ± 0.03* |
| Compound 1 | 0.045 | 10 | 12.8 ± 0.2* | 0.45 ± 0.07*& | 0.19 ± 0.08 | 0.52 ± 0.092* | 0.10 ± 0.04& |
| | 0.14 | | 10.5 ± 0.2*& | 0.41 ± 0.10*& | 0.07 ± 0.01 | 0.43 ± 0.076* | 0.13 ± 0.04& |
| | 14 | | 14.6 ± 0.3* | 0.45 ± 0.12*& | 0.15 ± 0.03* | 0.7 ± 0.16* | 0.15 ± 0.026*& |
| Experiment No. 2 | | | | | | | |
| Intact | — | | 0.02 ± 0.003 | 0.02 ± 0.003 | 0.05 ± 0.007 | 0.05 ± 0.001 | 0.07 ± 0.01 |
| Control | — | | 0.14 ± 0.02* | 0.67 ± 0.07* | 0.11 ± 0.003 | 0.49 ± 0.09* | 0.16 ± 0.02* |
| Compound 2 | 0.14 | 6 | 0.55 ± 0.09*& | 0.20 ± 0.03*& | 0.03 ± 0.008*& | 0.24 ± 0.06*& | 0.07 ± 0.02& |
| | 1.4 | | 0.63 ± 0.09*& | 0.18 ± 0.02*& | 0.09 ± 0.002 | 0.29 ± 0.07* | 0.06 ± 0.01& |
| | 14 | | 0.56 ± 0.008*& | 0.21 ± 0.06*& | 0.07 ± 0.002 | 0.22 ± 0.05*& | 0.07 ± 0.009& |

Note:
*difference from the intact group, according to Student's t-test, $p < 0.05$
&difference from the control group, according to Student's t-test, $p < 0.05$ The studied compounds reduced eosinophilia in the blood. In the control group, the eosinophil count in the blood was from 6 to 8 times higher than in the intact animals. The administration of the studied compounds allowed for remaining the count at the level of the intact animals (see Table 6).

TABLE 6

Content of cell elements in the blood in the model of bronchial asthma in guinea pigs
(M ± m, n = 8)

| Group | Dose of compound, mg/kg | Times of administration | Cytosis, $10^9$/L | Banded neutrophils, $10^9$/L | Segmented neutrophils, $10^9$/L | Eosinophils, $10^9$/L | Basophils, $10^9$/L | Monocytes $10^9$/L | Lymphocytes, $10^9$/L |
|---|---|---|---|---|---|---|---|---|---|
| Experiment No. 1 | | | | | | | | | |
| Intact | — | | 6.09 ± 0.68 | 0.08 ± 0.02 | 2.29 ± 0.35 | 0.08 ± 0.04 | 0 ± 0 | 0.10 ± 0.04 | 2.66 ± 0.49 |
| Control | — | | 12.51 ± 0.68* | 0.37 ± 0.11 | 3.92 ± 0.43 | 0.46 ± 0.06* | 0 ± 0 | 0.58 ± 0.16* | 7.45 ± 0.62* |
| Compound 1 | 0.045 | 10 | 9.03 ± 1.40& | 0.31 ± 0.10 | 2.92 ± 0.65 | 0.19 ± 0.04& | 0 ± 0 | 0.29 ± 0.08 | 4.80 ± 0.84* |
|  | 0.14 |  | 9.11 ± 1.07*& | 0.19 ± 0.05& | 2.23 ± 0.58& | 0.09 ± 0.03& | 0 ± 0 | 0.33 ± 0.06* | 5.25 ± 0.89* |
|  | 14 |  | 8.90 ± 0.25*& | 0.27 ± 0.06* | 3.66 ± 0.22* | 0.13 ± 0.04& | 0 ± 0 | 0.33 ± 0.06* | 4.45 ± 0.25* |
| Experiment No. 2 | | | | | | | | | |
| Intact | — | | 5.89 ± 0.31 | 0.14 ± 0.04 | 2.15 ± 0.26 | 0.05 ± 0.03 | 0 ± 0 | 0.15 ± 0.05 | 3.41 ± 0.32 |
| Control | — | | 13.26 ± 0.55* | 0.33 ± 0.11 | 5.34 ± 0.71* | 0.39 ± 0.07* | 0 ± 0 | 0.38 ± 0.09* | 6.81 ± 0.49* |
| Compound 2 | 0.14 | 6 | 7.80 ± 0.77*& | 0.18 ± 0.04 | 3.41 ± 0.41*& | 0.09 ± 0.03& | 0 ± 0 | 0.18 ± 0.06 | 3.95 ± 0.54& |
|  | 1.4 |  | 7.70 ± 0.40*& | 0.21 ± 0.03 | 3.53 ± 0.37*& | 0.1 ± 0.03& | 0 ± 0 | 0.18 ± 0.06 | 3.68 ± 0.25& |
|  | 14 |  | 6.93 ± 0.77& | 0.17 ± 0.04 | 2.9 ± 0.38& | 0.1 ± 0.04& | 0 ± 0 | 0.24 ± 0.08 | 3.51 ± 0.41& |

Note:
*difference from the intact group, according to Student's t-test, $p < 0.05$
&difference from the control group, according to Student's t-test, $p < 0.05$ The evaluation of the severity of bronchospasm in the guinea pigs in response to inhalation of the challenging dose of ovalbumin showed that in the model of bronchial asthma, the studied compounds reduced not only eosinophilia but also clinical manifestations of the disease. In particular, in the control group received placebo, five among eight animals had severe bronchospasm with acute and subacute phase; such animals either were absent in the group of animals received the studied compounds or their number was not more than two animals. In turn, the number of animals with the normal rate and depth of breathing (without bronchospasm) increased from 0-1 in the control group to 4-7 in the groups received the treatment (see Table 7).

Example 5

Evaluation of the Efficiency of the Compounds of General Formula (I) in a Model of Sephadex-induced Eosinophilic Lung Inflammation in Rats The model of sephadex-induced eosinophilic lung inflammation in rats was realized by a standard method [Evaldsson C, Rydén I, Uppugunduri S. Isomaltitol exacerbates neutrophilia but reduces eosinophilia: new insights into the sephadex model of lung inflammation//Int Arch Allergy Immunol. 2011; 154(4):286-94]. Sephadex G-200 (Pharmacia,

TABLE 7

Severity of bronchospasm in the model of bronchial asthma in guinea pigs

| Group | Dose of compound, mg/kg | Tines of administration | The number of animals (n = 8) | | | |
|---|---|---|---|---|---|---|
| | | | without bronchospasm | with moderate bronchospasm (without acute phase, with subacute phase, with breath management) | with moderate bronchospasm (without acute phase, with subacute phase, without breath management) | With severe bronchospasm (in acute and subacute phase) |
| Experiment No. 1 | | | | | | |
| Intact | — | | 8 | 0 | 0 | 0 |
| Control | — | | 0 | 0 | 3 | 5 |
| Compound 1 | 0.045 | 10 | 5 | 1 | 2 | 0 |
|  | 0.14 |  | 7 | 1 | 0 | 0 |
|  | 14 |  | 5 | 0 | 2 | 1 |
| Experiment No. 2 | | | | | | |
| Intact | — | | 8 | 0 | 0 | 0 |
| Control | — | | 1 | 1 | 1 | 5 |
| Compound 2 | 0.14 | 6 | 4 | 1 | 1 | 2 |
|  | 1.4 |  | 4 | 0 | 3 | 1 |
|  | 14 |  | 5 | 1 | 0 | 2 |

The obtained results give reliable evidences that in the experimental models of eosinophilia, in particular of bronchial asthma and the like, the claimed compounds suppress eosinophilia and reduce clinical manifestations of the disease.

Sweden) was administered one time by inhalation to male Wistar rats at a dose of 5 mg/kg. The studied compounds were administered to the animals by the intragastric route four times: 24 hours and 1 hour before and 24 hours and 45 hours after administration of sephadex. The reference preparation, budesonide, was administered according to the same scheme, by inhalation at a dose of 0.5 mg/kg. Bronchoalveolar lavage was taken 48 hours after the inhalation of sephadex, and the total lymphocyte count and leukocyte formula in the lavage were determined. The number of rats in a group was 7 to 10.

The analysis of the BAL showed that one time administration of sephadex G-200 by inhalation caused an apparent flow of leukocytes into the lung. The content of all cell types was increased in the control group relative to the intact animals; however, the maximum increase was registered for eosinophils (see Tables 8-9).

The intragastric administration of the compounds of formula (I) to the rats reduced the eosinophil count in the BAL by several times. The claimed compounds exhibited activity within a broad range of the tested doses.

leukotriene (LT) D4 administration in the guinea pig: modulation by the LTD4 receptor antagonist, pranlukast, or an interleukin-5 monoclonal antibody// Am J Respir Crit Care Med. 1996 October; 154(4 Pt 1):850-7]. A solution of leukotriene D4 (LTD4, Cayman Chemical, USA) at a concentration of 10 mg/kg (a flow rate of 250 mL/hr) was inhaled to male guinea pigs (250-300 g) under conditions of a double-chamber plethysmograph (Emka Technologies, France) for one minute. The studied compound was administered to the animals by the intragastric route four times: 24 hours and 1 hour before and 24 hours and 45 hours after the inhalation of LTD4. The reference preparation, montelukast (0.8 mg/kg), was administered one time by the intragastric route one hour before the inhalation of LTD4. Bronchoalveolar lavage was taken 48 hours after the inhalation of

TABLE 8

Content of cell elements in BAL in the model of sephadex-induced eosinophilic lung inflammation in rats (M ± m, n = 10)

| Group | Content of cell elements in 1 µL of BAL | | | | |
|---|---|---|---|---|---|
|  | Leukocytes | Neutrophils | Eosinophils | Macrophages | Lymphocytes |
| Intact | 865 ± 78 | 35 ± 9 | 13 ± 4 | 770 ± 66 | 46 ± 12 |
| Control | 2785 ± 152* | 711 ± 158* | 444 ± 45* | 1469 ± 197* | 161 ± 44* |
| Compound 1 (0.06 mg/kg) | 2500 ± 307* | 837 ± 231* | 118 ± 27*& | 1417 ± 131* | 128 ± 48 |
| Compound 1 (0.18 mg/kg) | 2665 ± 455* | 597 ± 168* | 174 ± 64*& | 1661 ± 260* | 143 ± 54 |
| Compound 1 (0.54 mg/kg) | 2120 ± 218*& | 352 ± 135* | 126 ± 43*& | 1446 ± 113* | 196 ± 63* |
| Compound 1 (1.8 mg/kg) | 1915 ± 250*& | 451 ± 149* | 129 ± 44*& | 1214 ± 130* | 122 ± 49 |
| Compound 1 (5.4 mg/kg) | 2340 ± 322* | 492 ± 129* | 152 ± 56*& | 1525 ± 199* | 170 ± 45* |
| Compound 1 (18 mg/kg) | 2135 ± 205*& | 297 ± 89*& | 69 ± 22*& | 1601 ± 134* | 168 ± 44* |
| Budesonide (0.5 mg/kg) | 1805 ± 318*& | 334 ± 119* | 204 ± 84*& | 1230 ± 205 | 37 ± 10& |

Note:
*difference from the intact group, according to Student's t-test, $p < 0.05$
&difference from the control group, according to Student's t-test, $p < 0.05$

TABLE 9

Content of cell elements in BAL in the model of sephadex-induced eosinophilic lung inflammation in rats (M ± m, n = 7)

| Group | Content of cell elements in 1 µL of BAL | | | | |
|---|---|---|---|---|---|
|  | Leukocytes | Neutrophils | Eosinophils | Macrophages | Lymphocytes |
| Intact | 2471 ± 611 | 150 ± 63 | 39 ± 31 | 1532 ± 225 | 31 ± 26 |
| Control | 5207 ± 814* | 785 ± 163* | 630 ± 104* | 3471 ± 412* | 275 ± 103 |
| Compound 5 (1.8 mg/kg) | 2064 ± 257& | 385 ± 57* | 147 ± 44& | 1576 ± 93& | 66 ± 26 |
| Compound 5 (18 mg/kg) | 2189 ± 222& | 605 ± 124 | 34 ± 15& | 1331 ± 66 & | 121 ± 48 |
| Compound 7 (1.8 mg/kg) | 2242 ± 289& | 389 ± 188 | 28 ± 16& | 913 ± 235& | 16 ± 10 |
| Compound 7 (18 mg/kg) | 1725 ± 345& | 136 ± 50& | 164 ± 62 & | 909 ± 299& | 29 ± 17 |
| Compound 8 (1.8 mg/kg) | 2796 ± 333 & | 303 ± 104& | 202 ± 53*& | 1860 ± 204& | 82 ± 44 |
| Compound 8 (18 mg/kg) | 4250 ± 576 | 583 ± 180 | 318 ± 65*& | 2050 ± 462& | 64 ± 45 |

Note:
*difference from the intact group, according to Student's t-test, $p < 0.05$
&difference from the control group, according to Student's t-test, $p < 0.05$ Example 6

Evaluation of the Efficiency of the Compounds of General Formula (I) in a Model of Leukotriene-induced Eosinophilic Lung Inflammation in Guinea Pigs The model of leukotriene-induced eosinophilic lung inflammation in guinea pigs was realized by a standard method [Underwood DC1, Osborn R R, Newsholme S J, Torphy T J, Hay D W. Persistent airway eosinophilia after LTD4, and the total lymphocyte count and leukocyte formula were determined in the lavage. The number of guinea pigs in a group was 8.

The analysis of BAL showed that one time administration of leukotriene D4 to guinea pig by inhalation caused an apparent flow of neutrophils, eosinophils, and monocytes/macrophages into the lungs. The most evident increase in the cell count (25 times) was observed for eosinophils (see Table 10).

The intragastric administration of the studied compound to the guinea pigs reduced the eosinophil count in the BAL by 2.1-3.4 times. The compounds had an effect within a broad range of doses (0.14-14 mg/kg). The comparative analysis of the efficiency of the claimed compound and montelukast showed that the effects of the claimed compound and the leukotriene receptor agonist were comparable by strength.

solution of aluminium hydroxide (5 mg/pig), and on days 28 and 35, they received a physiological saline solution, and on day 42, a solution of ovalbumin (60 mg/mL, 20 µL/nostril).

The studied compounds (14 mg/kg) were administered 3 times by the intragastric route: 48, 24, and 1 hour before the last administration of ovalbumin. The reference preparation, dexamethasone, was administered one time by the intragastric route, 3 hours before the last intranasal administration of ovalbumin.

Clinical manifestations, such as the number of sneezes and nose scratchings, were registered for 2 hours after the last administration of ovalbumin. Nasal lavage was taken 24 hours after the last administration of ovalbumin, and in this lavage, the total lymphocyte count and leukocyte formula were determined. The number of guinea pigs in a group was 8.

The analysis of the nasal lavage showed that allergic rhinitis is accompanied by an apparent flow of leukocytes into the nasal cavity. The maximum increase was registered for eosinophils (Table 11).

Three-time administration of the compounds of general formula (I) to the guinea pigs reduced the eosinophil count in the nasal lavage to the level observed in the pseudoimmunized animals. The effects of the claimed compound and dexamethasone were comparable by strength.

TABLE 10

Content of cell elements in BAL in the model of leukotriene-induced eosinophilic lung inflammation in guinea pigs (M ± m, n = 8)

| Group | Content of cell elements in 1 µL of BAL | | | | |
|---|---|---|---|---|---|
| | Leukocytes | Neutrophils | Eosinophils | Macrophages | Lymphocytes |
| Intact | 556 ± 83 | 21 ± 4 | 79 ± 26 | 357 ± 55 | 100 ± 32 |
| Control | 5788 ± 1269* | 303 ± 66* | 1966 ± 391* | 3392 ± 895* | 126 ± 35 |
| Compound 1 (0.14 mg/kg) | 2638 ± 463*& | 249 ± 50 | 916 ± 144*& | 1360 ± 323* | 112 ± 27 |
| Compound 1 (1.4 mg/kg) | 3413 ± 1022* | 279 ± 97* | 856 ± 288*& | 2134 ± 705* | 144 ± 89 |
| Compound 1 (14 mg/kg) | 2250 ± 373*& | 155 ± 36* | 580 ± 124*& | 1444 ± 258* | 71 ± 28 |
| Montelukast (0.8 mg/kg) | 24065 ± 415*& | 173 ± 41* | 618 ± 116*& | 1519 ± 263* | 96 ± 39 |

Note:
*difference from the intact group, according to Student's t-test, $p < 0.05$
&difference from the control group, according to Student's t-test, $p < 0.05$ Example 7

Evaluation of the Efficiency of the Compounds of General Formula (I) in a Model of Allergic Rhinitis in Guinea Pigs The model of allergic rhinitis in guinea pigs was realized by a standard method [Vishnu N. Thakare, M. M. Osama, Suresh R. Naik. Therapeutic potential of curcumin in experimentally induced allergic rhinitis in guinea pigs // Int Immunopharmacol. 2013 September; 17(1):18-25].

Guinea pigs (250-300 g) were immunized with 4-time (on days 0, 7, 14, and 21) intragastric administration of ovalbumin (100 µg/pig) and aluminium hydroxide (5 mg/pig), both of which were diluted and suspended in a physiological saline solution. On day of the study, a solution of ovalbumin (60 mg/mL) was administered intranasally to each nostril of the animals at a dose 20 µL. On day 35, the animals received subcutaneously an ovalbumin solution (200 µg/mL, 25 µL); the animal back was previously shaved in the site of administration. Swelling and redness at the injection site served as a support of sensibilisation. On day 42 of the study, an ovalbumin solution (60 mg/mL, 20 µL/nostril) was administered intranasally. A group of pseudoimmunized animals was formed to control the formation of exactly allergic inflammation: on days 0, 7, 14, and 21, the pigs received a

TABLE 11

Content of cell elements in the nasal lavage of in guinea pigs in the model of allergic rhinitis (M ± m, n = 8)

| Group | Content of cell elements in 1 µL of nasal lavage | | | | |
|---|---|---|---|---|---|
| | Leukocytes | Neutrophils | Eosinophils | Macrophages | Lymphocytes |
| Pseudoimmunization | 1371 ± 181 | 424 ± 30 | 267 ± 38 | 712 ± 125 | 8 ± 6 |
| Control | 3029 ± 286* | 753 ± 121* | 1265 ± 226* | 439 ± 132 | 8 ± 8 |
| Compound 1 (14 mg/kg) | 1300 ± 254& | 243 ± 58*& | 521 ± 129& | 405 ± 130 | 6 ± 6 |
| Compound 5 (14 mg/kg) | 1071 ± 233& | 344 ± 50& | 575 ± 143& | 198 ± 54* | 9 ± 7 |
| Dexamethasone (5 mg/kg) | 1186 ± 142& | 328 ± 47& | 365 ± 90& | 296 ± 71* | 5 ± 3 |

Note:
*difference from the intact group, according to Student's t-test, $p < 0.05$
&difference from the control group, according to Student's t-test, $p < 0.05$ The registration of clinical manifestations of allergic rhinitis for 2 hours after the last intranasal administration of ovalbumin showed an apparent increase in the number of sneezes and nose scratchings in the experimental animals, which was indicative of the correctness of the realized model of allergic rhinitis. The therapy with the compounds of general formula (I) reduced the clinical manifestations of rhinitis to their level observed in the pseudoimmunized animals. The reference preparation had a similar effect (see Table 12).

TABLE 12

Clinical manifestations of allergic rhinitis in guinea pigs in the experimental model (M ± m, n = 8)

| Group | Number of sneezes/2 hours | Number of nose scratchings/2 hours |
|---|---|---|
| Pseudoimmunization | 5.3 ± 1.2 | 9.7 ± 1.3 |
| Control | 16.3 ± 2.6* | 45.3 ± 5.2* |
| Compound 1 (14 mg/kg) | 5.9 ± 1.1 & | 13.9 ± 2.6 & |
| Compound 5 (14 mg/kg) | 7.1 ± 1.3 & | 19.1 ± 4.9 & |
| Dexamethasone (5 mg/kg) | 7.9 ± 0.8 & | 16.7 ± 1.8*& |

Notes:
*difference from the intact group, according to Student's t-test, p < 0.05
& difference from the control group, according to Student's t-test, p < 0.05

Example 8

Evaluation of the Efficiency of the Compounds of General Formula (I) in a Model of Allopathic Dermatitis in Mice The model of allopathic dermatitis was realized by a standard method [Mechanism of dinitrochlorobenzene-induced dermatitis in mice: role of specific antibodies in pathogenesis//PLoS One. 2009; 4(11)].
On days 0 and 12 of the study, 100 µL of a 2% solution of 1-chloro-2,4-dinitrobenzene (DNCB, Sigma-Aldrich, US) in 95% ethanol was applied to shaved sites in the backs of male Balb/c mice. On day 17 of the study, to the right "studied" ear of the animals, 20 µL of the alcohol solution of 2% DNCB was applied two times with a one-hour interval. The studied compound and the reference preparation, dexamethasone, were administered by the intragastric route once daily on days 8-17 of the study.
On day 18 of the study, the animals were euthanized in a CO2 camera. The weights of the "studied" and "control" ears were measured. A response index (RI) expressed in percentage of a difference in the weights of the "studied" and "control" ears was calculated.
The study showed that the compounds of general formula (I) reduced the response index in the experimental model of atopic dermatitis. The effects of the claimed compound and of the steroid preparation, dexamethasone, were comparable by strength (see Table 13).

TABLE 13

Response index in atopic dermatitis in mice (M ± m, n = 12)

| Group | Response index (%) |
|---|---|
| Intact | −0.49 ± 0.68 |
| Control | 93.8 ± 5.4* |
| Compound 1 (0.3 mg/kg) | 74.4 ± 7.3*& |
| Compound 1 (3 mg/kg) | 69.5 ± 8.2*& |
| Compound 1 (30 mg/kg) | 69.1 ± 8*& |
| Dexamethasone (10 mg/kg) | 65.6 ± 8*& |

Notes:
*difference from the intact group, according to Student's t-test, p < 0.05
&difference from the control group, according to Student's t-test, p < 0.05

The obtained results give grounds for a conclusion that in the experimental models of eosinophilia, in particular sep-hadex-induced eosinophilic lung inflammation in rats, leukotriene-induced eosinophilic lung inflammation in guinea pigs, allergic rhinitis and asthma in guinea pigs, atopic dermatitis in mice, and the like, the compounds of general formula (I) significantly reduce eosinophilia.

What is claimed is:

1. A method of treating an eosinophilic disease, the method comprising administering to a patient of an effective amount of a compound of the formula

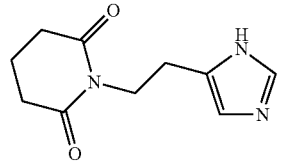 [SMILES: O=C1CCCC(=O)N1CCc1cnc[nH]1]

or a pharmaceutically acceptable salt thereof,
wherein the eosinophilic disease is selected from the group consisting of bronchial asthma, allergic rhinitis, polypous rhinosinusopathies, atopic dermatitis, and eosinophilic esophagitis, and
wherein eosinophils in the patient are reduced.

2. The method of claim 1, wherein the pharmaceutically acceptable salt is a salt of an organic acid, a salt of an inorganic acid, or a salt of an amino acid.

3. The method of claim 2, wherein the salt of the organic acid is a formate salt, an acetate salt, a maleate salt, a tartrate salt, a methanesulfonate salt, a benzenesulfonate salt, or a toluenesulfonate salt.

4. The method of claim 2, wherein the salt of the inorganic acid is a hydrochloride salt, a hydrobromide salt, a sulfate salt, or a phosphate salt.

5. The method of claim 2, wherein the salt of the amino acid is an aspartic acid salt or a glutamic acid salt.

6. The method of claim 1, wherein the pharmaceutically acceptable salt is a chlorohydrate or an acetate.

7. The method of claim 1, wherein the administering of the compound or pharmaceutically acceptable salt thereof is carried out by an administration route selected from the group consisting of oral, topical, parenteral, intranasal, sublingual, inhalational, and rectal.

8. The method of claim 7, wherein the administration route is parenteral and the compound is administered subcutaneously, intravenously, intramuscularly, by injection, or by infusion.

9. The method of claim 1, wherein the administering of the compound or pharmaceutically acceptable salt thereof is carried out at a dose of from about 0.1 to about 30 mg/kg of body weight of the patient.

10. The method of claim 9, wherein the dose is from about 0.25 to about 10 mg/kg of body weight of the patient.

11. The method of claim 9, wherein the dose is administered one or more times per day.

12. The method of claim 11, wherein the dose is administered once daily.

13. The method of claim 1, wherein the compound or pharmaceutically acceptable salt thereof is administered in a pharmaceutical composition, further comprising a pharmaceutically acceptable carrier.

14. The method of claim 13, wherein the pharmaceutical composition is in a form selected from the group consisting of a solution, a tablet, a pill, a capsule, a dragee, a suppository, an emulsion, a suspension, an ointment, and a gel.

15. The method of claim 14, wherein the pharmaceutical composition is in the form of a pill, coated with a layer that is resistant to gastric acid.

16. The method of claim 13, wherein the pharmaceutically acceptable carrier selected from the group consisting of glucose, lactose, sucrose, mannitol, sorbitol, a cellulose derivative, and a calcium phosphate.

17. The method of claim 13, wherein the pharmaceutical composition further comprises a binder.

\* \* \* \* \*